US008066904B2

United States Patent
Fine et al.

(10) Patent No.: US 8,066,904 B2
(45) Date of Patent: Nov. 29, 2011

(54) CONTROLLED GENERATION OF NITRIC OXIDE

(75) Inventors: David H. Fine, Lincoln, MA (US); Stephen J. MacDonald, Salem, NH (US); David Rounbehler, West Harwich, MA (US); David Wheeler, Lunenburg, MA (US); Jonathan L. Rolfe, N. Easton, MA (US); George Jarvis, Arlington, MA (US)

(73) Assignee: Geno LLC, Cocoa, FL (US)

( * ) Notice: Subject to any disclaimer, the term of this patent is extended or adjusted under 35 U.S.C. 154(b) by 1904 days.

(21) Appl. No.: 10/228,956

(22) Filed: Aug. 28, 2002

(65) Prior Publication Data

US 2003/0064028 A1    Apr. 3, 2003

Related U.S. Application Data

(60) Provisional application No. 60/316,964, filed on Sep. 5, 2001.

(51) Int. Cl.
*A61K 33/00* (2006.01)
*A61K 33/24* (2006.01)
*A61K 33/30* (2006.01)
*A61K 33/34* (2006.01)
*A61K 9/00* (2006.01)
*A61K 9/20* (2006.01)
*A61M 16/10* (2006.01)
*C09K 3/00* (2006.01)

(52) U.S. Cl. .............. 252/186.44; 252/182.34; 424/718; 424/485; 424/486; 424/487; 424/488; 424/499

(58) Field of Classification Search .............. 252/186.44
See application file for complete search history.

(56) References Cited

U.S. PATENT DOCUMENTS

| | | | |
|---|---|---|---|
| 1,021,234 A | | 3/1912 | Muller von Berneck et al. |
| 2,272,810 A | * | 2/1942 | Milburn .......................... 8/452 |
| 4,007,057 A | | 2/1977 | Littauer et al. |
| 4,010,897 A | | 3/1977 | Treharne et al. |
| 4,287,040 A | | 9/1981 | Alamaro |
| 4,774,069 A | | 9/1988 | Handley |
| 4,778,450 A | | 10/1988 | Kamen |
| 5,228,434 A | | 7/1993 | Fishman |
| 5,396,882 A | | 3/1995 | Zapol |
| 5,485,827 A | | 1/1996 | Zapol et al. |
| 5,525,357 A | | 6/1996 | Keefer et al. |

(Continued)

FOREIGN PATENT DOCUMENTS

WO    WO 94/16740    8/1994

(Continued)

OTHER PUBLICATIONS

Mascarenhas, Oscar Carlton, "Epoxy-Based Medical Grade Adhesive Hydrogels and Nitric Oxide Releasing Polymers", *Dissertation Abstracts International*, vol. 55/02-B, pp. 445 (1993).

(Continued)

*Primary Examiner* — Joseph D Anthony
(74) *Attorney, Agent, or Firm* — Steptoe & Johnson LLP

(57) ABSTRACT

Inhalation of low levels of nitric oxide can rapidly and safely decrease pulmonary hypertension in mammals. Precise delivery of nitric oxide at therapeutic levels of 20 to 100 ppm and inhibition of reaction of nitric oxide with oxygen to form toxic impurities such as nitrogen dioxide can provide effective inhalation therapy for pulmonary hypertension.

6 Claims, 4 Drawing Sheets

U.S. PATENT DOCUMENTS

| | | | |
|---|---|---|---|
| 5,545,614 A | 8/1996 | Stamler et al. | |
| 5,558,083 A | 9/1996 | Bathe et al. | |
| 5,570,683 A | 11/1996 | Zapol | |
| 5,615,669 A | 4/1997 | Olsson et al. | |
| 5,648,101 A * | 7/1997 | Tawashi | 424/718 |
| 5,651,358 A | 7/1997 | Briend et al. | |
| 5,676,963 A | 10/1997 | Keefer et al. | |
| 5,683,668 A | 11/1997 | Hrabie et al. | |
| 5,692,495 A | 12/1997 | Sheu | |
| 5,823,180 A | 10/1998 | Zapol | |
| 5,827,420 A | 10/1998 | Shirazi et al. | |
| 5,839,433 A | 11/1998 | Higenbottam | |
| 5,871,009 A | 2/1999 | Rydgren et al. | |
| 5,873,359 A | 2/1999 | Zapol et al. | |
| 5,994,444 A | 11/1999 | Trescony et al. | |
| 6,046,383 A * | 4/2000 | Elsenga-Boersma et al. | 800/274 |
| 6,103,275 A * | 8/2000 | Seitz et al. | 424/718 |
| 6,109,260 A | 8/2000 | Bathe | |
| 6,158,434 A | 12/2000 | Lugtigheid et al. | |
| 6,190,704 B1 | 2/2001 | Murrell | |
| 6,261,594 B1 | 7/2001 | Smith et al. | |
| 6,270,779 B1 | 8/2001 | Fitzhugh et al. | |
| 6,758,214 B2 | 7/2004 | Fine et al. | |
| 7,025,869 B2 * | 4/2006 | Fine et al. | 205/553 |
| 7,040,313 B2 * | 5/2006 | Fine et al. | 128/203.12 |
| 2001/0012851 A1 | 8/2001 | Lundy et al. | |
| 2002/0090401 A1 * | 7/2002 | Tucker et al. | 424/718 |
| 2005/0142218 A1 * | 6/2005 | Tucker et al. | 424/718 |
| 2009/0081279 A1 * | 3/2009 | Jezek et al. | 424/445 |
| 2009/0297634 A1 * | 12/2009 | Friedman et al. | 424/718 |

FOREIGN PATENT DOCUMENTS

| WO | WO 01/15738 A2 | 3/2001 |
|---|---|---|

OTHER PUBLICATIONS

Pulfer, Sharon Kay, "Nitric Oxide Releasing Polymers and Their Application to Vascular Devices (Polyethyleneimine, Polytetrafluoroethylene)", *Dissertation Abstracts International*, vol. 56/12-B, pp. 6727 (1995).

Roselle, Dominick C., et al., "Characterization and Nitric Oxide Release Studies of Lipophilic 1-Substituted Diazen-1-ium-1,2-Diolates", *Journal of Controlled Release*, vol. 51, pp. 131-142 (1998).

Smith, Daniel J.,et al., "Nitric Oxide-Releasing Polymers Containing the [N(O)NO]⁻Group", *Journal of Medicinal Chemistry*, vol. 39, No. 5, pp. 1148-1156 (1996).

Taira, Masafumi, et al. "Continuous Generation System for Low-Concentration Gaseous Nitrous Acid", *Analytical Chemistry*, vol. 62, No. 6, pp. 630-633, (1990).

Suzuki, "Nitrogen Oxides Generation Method for Recovered Nitric Acid by Electrolysis. An Action Plan for Reduction of Low-Level-Liquid-Waste in Processing Plant", Kyoto Daigaku Genshiro Jikkensho, (Tech. Rep.) (no month, 1991), KURRI-TR-361, pp. 19-26.

Non-final Office Action dated Apr. 8, 2005 for U.S. Appl. No. 10/229,026, filed Aug. 28, 2002; 17 pages.

International Search Report, 8 pages, Mar. 10, 2004.

Tannenbaum, S.R. et al., "Inhibition of Nitrosamine Formation by Ascorbic Acid," *The American Journal of Clinical Nutrition*, American Society of Clinical Nutrition, Bethesda, Maryland, Jan. 1991, vol. 53, pp. 247-250.

Licht, W.R. et al., "Use of Ascorbic Acid to Inhibit Nitrosation: Kinetic and Mass Transfer Considerations for an in Vitro System," *Carcinogenesis*, IRL Press At Oxford University Press, Oxford, Mar. 1988, pp. 365-371.

* cited by examiner

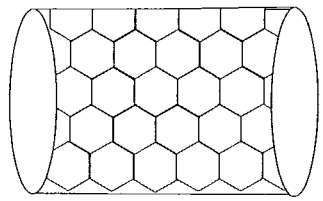
FIG. 2E
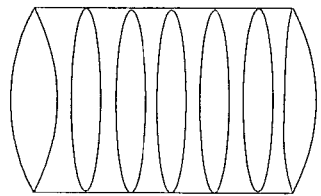
FIG. 2I
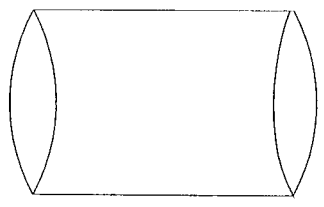
FIG. 2D
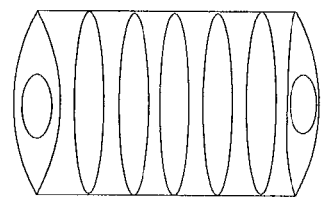
FIG. 2H
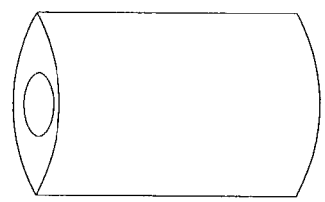
FIG. 2C
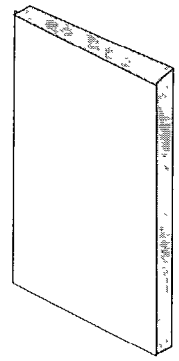
FIG. 2G
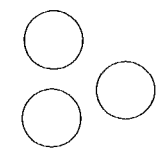
FIG. 2B
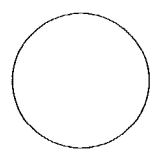
FIG. 2A
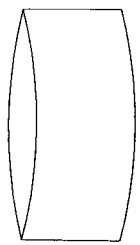
FIG. 2F
FIG. 2

CONTROLLED GENERATION OF NITRIC OXIDE

CLAIM OF PRIORITY

This application claims the benefit of U.S. Application No. 60/316,964 filed on Sep. 5, 2001, which is incorporated by reference in its entirety.

CROSS REFERENCE TO RELATED APPLICATIONS

The present application is related to co-pending application Ser. No. 10/228,958 entitled "Method and Apparatus For Generation of Nitric Oxide," filed concurrently herewith, and co-pending application Ser. No. 10/229,026 entitled "Nitric Oxide Delivery System," also filed concurrently herewith, each of which is incorporated by reference in its entirety.

TECHNICAL FIELD

This invention relates to an apparatus and a method for controllably generating nitric oxide.

BACKGROUND

Nitric oxide plays an important role in the regulation of biochemical pathways in living organisms. The inhalation of low levels (20 to 100 ppm) of nitric oxide has been shown to have a major therapeutic value in treatment of a diverse range of disorders ranging from reversible and irreversible pulmonary hypertension to treatment of neonates exhibiting hypoxemic respiratory failure and persistent pulmonary hypertension. Conventional medical uses of nitric oxide gas can involve dilution of a nitric oxide gas stream with gases immediately before administration of the nitric oxide gas to a mammal. Precise delivery of nitric oxide at therapeutic levels of 20 to 100 ppm and inhibition of reaction of nitric oxide with oxygen to form toxic impurities such as nitrogen dioxide gas is needed for effective inhalation therapy.

SUMMARY

Nitric oxide, also known as nitrosyl radical, is a free radical that is an important signaling molecule in pulmonary vessels. Nitric oxide can moderate pulmonary hypertension caused by elevation of the pulmonary arterial pressure. Inhaling low concentrations of nitric oxide, for example, in the range of 20-100 ppm can rapidly and safely decrease pulmonary hypertension in a mammal by vasodilation of pulmonary vessels.

Some disorders or physiological conditions can be mediated by inhalation of nitric oxide. The use of low concentrations of inhaled nitric oxide can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide can also be used to treat chronic pulmonary hypertension, bronchopulmonary dysplasia, chronic pulmonary thromboembolism and idiopathic or primary pulmonary hypertension or chronic hypoxia. Advantageously, nitric oxide can be generated and delivered in the absence of harmful side products, such as nitrogen dioxide. The nitric oxide can be generated at a concentration suitable for delivery to a mammal in need of treatment.

A nitric oxide delivery system can be a controlled drug delivery system, which produces steady-state levels of nitric oxide. The system can provide for zero-order, first order and second order drug release kinetics. Controlled drug delivery devices can provide a constant level of pharmaceutical drug to a mammal which can optimize the drug input rate into the systemic circulation, improve mammal compliance, minimize side effects, and maximize drug product efficacy.

Controlled nitric oxide delivery can include controlling the diffusion/dissolution of the nitric oxide. The nitric oxide precursor composition can include a matrix and a contained phase of a nitric oxide precursor, for slow or controlled release of nitric oxide into the surrounding or external medium. Controlling the release of nitric oxide can result in greater longevity of the nitric oxide precursor and longer availability of the nitric oxide precursor for its intended purpose while providing a means for greater control in the concentration of nitric oxide into the surrounding medium.

In one aspect, a nitric oxide generating composition includes a nitric oxide precursor contained within a matrix. The matrix can be non-reactive with the nitric oxide precursor. The matrix can be a hydrogel, for example, a urethane. The matrix can be a hydrophilic polymer, for example, a polysaccharide. The nitric oxide precursor can be a nitrite salt, for example, sodium nitrite. The matrix can be in a shape which includes a sphere, a monolith or a three-dimensional object. The three-dimensional object can be a cylinder or a film. The matrix can further include an additive, for example, a polymer, a salt, a filler or a solvent.

In another aspect, a method of administering nitric oxide to a mammal includes generating a therapeutic gas including nitric oxide from a nitric oxide precursor contained in a matrix that is non-reactive with the precursor and transporting the therapeutic gas in a transport gas stream to the mammal. The nitric oxide precursor can be contacted with a reaction solution to form a mixture. The nitric oxide precursor can be a nitrite salt. The nitrite salt can be, for example, sodium nitrite. The transport gas can be swept over the mixture. The therapeutic gas can deliver, for example, 20 to 60 ppm nitric oxide to the mammal. The transport gas can be oxygen, ambient air or a mixture of air and oxygen. The nitric oxide can be released from the precursor for over at least an hour. The therapeutic gas can be substantially devoid of nitrogen dioxide.

In another aspect, a unitary structure includes a mixture of a matrix and a plurality of nitric oxide precursor particles contained in the matrix.

In another aspect, a method of manufacturing a unitary structure for delivering nitric oxide includes combining a matrix and a plurality of nitric oxide precursor particles to form a mixture and shaping the mixture to form a unitary structure.

In another aspect, a process for preparing a formulation for delivering nitric oxide includes combining a plurality of the nitric oxide precursor particles within a hydrophilic matrix.

In another aspect, an electrophoresis apparatus for delivering nitric oxide to a patient includes a delivery portion, a reaction chamber in fluid communication with the delivery portion and a nitric oxide precursor receiving portion including an electrophoresis region bounded by a first electrode and a second electrode arranged to migrate a nitric oxide precursor to the reaction chamber when a voltage is applied across the first electrode and the second electrode. The nitric oxide precursor includes a precursor salt which can be a nitrite salt. The nitrite salt can be, for example, sodium nitrite.

In another aspect, a method of producing nitric oxide includes applying a voltage across a cavity including an electrophoresis region bound by a first electrode and a second electrode arranged to migrate a nitric oxide precursor in the electrophoresis region to a reaction chamber and contacting the nitric oxide precursor with a reaction solution in the reaction chamber to generate a therapeutic gas including nitric oxide. The method can include varying the voltage between the electrodes. The method can include varying the concentration of the nitric oxide precursor.

In another aspect, a kit includes a nitric oxide precursor and an instructional material describing a method of generating a therapeutic gas and transporting the therapeutic gas, the therapeutic gas comprising nitric oxide and being substantially devoid of nitrogen dioxide.

The hydrogel can include a polymer, for example, a urethane, a polysaccharide, a polyphosphazene, a polyacrylate, a block copolymer, a polyethylene oxide-polypropylene glycol block copolymer, a fibrin, a polyvinylpyrrolidone, a hyaluronic acid, a collagen or a polyethylene glycol.

The hydrophilic polymer can include a component, for example, guar gum, gum arabic, gum karaya, gum ghatti, locust bean gum, tamarind gum, agar, agarose, carageenan gum, pectin or gluten.

The composition can include a reaction solution. The reaction solution can include a pH buffer combination, for example, acetic acid/acetate, hydrochloric acid/chloride, hydrochloric acid/citrate, citric acid-phosphate, phosphoric acid/phosphate or citric acid/citrate. The reaction solution can include a nitric oxide releasing salt, for example, a ferrous salt. The pH of the mixture can be in the range of 4 to 7 or 6.5 to 6.9.

Other features or advantages will be apparent from the following detailed description of several embodiments, and also from the appended claims.

DESCRIPTION OF DRAWINGS

FIG. 2 is drawing depicting a schematic view of nitric oxide precursors.

DETAILED DESCRIPTION

Figure 1:
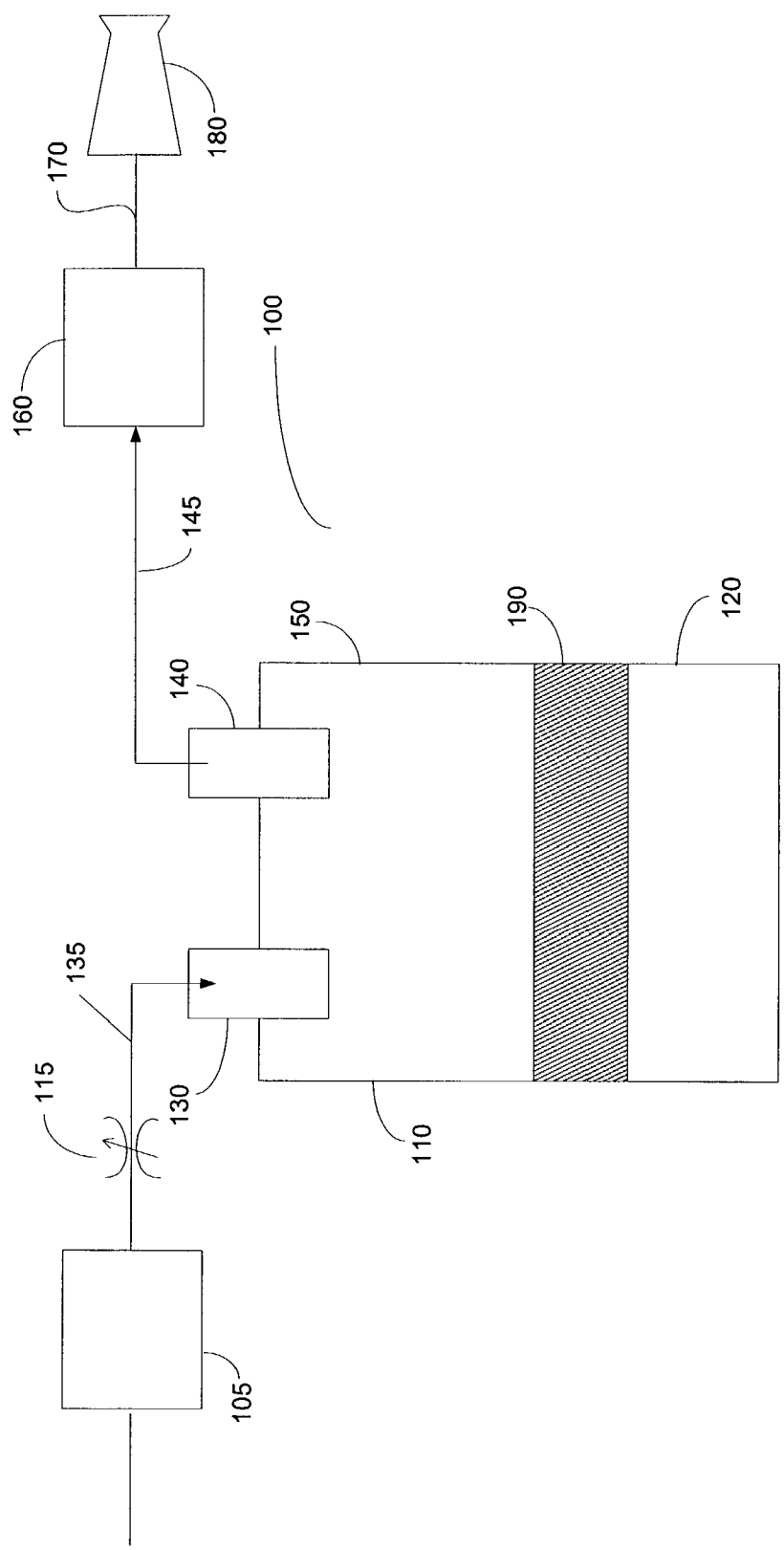
FIG. 1 is a drawing depicting a schematic view of a nitric oxide generation and delivery system.

Various nitric oxide precursors can be used in a nitric oxide delivery system. Nitric oxide precursors can include a nitrogen-containing compound with a structure X-nitric oxide, when X is an organic residue or a precursor salt. For example, the nitric oxide precursor can include an alkali metal nitrite, an alkaline earth metal nitrite, a transition metal nitrite or an ammonium nitrite, for example, potassium nitrite, sodium nitrite, rubidium nitrite, strontium nitrite, barium nitrite, calcium nitrite, copper nitrite, zinc nitrite, or mixtures thereof. The nitric oxide precursor can include nitrogen-containing acids, such as nitric acid. Physical characteristics of the nitric oxide precursor, such as the dissolution rate, can be used to control delivery of nitric oxide.

The nitric oxide precursor can be dissolved in a solution in which the precursor can dissociate to form anions, including nitrite anions, and cations. The solution can include a buffer solution. A buffer solution can include a pH buffer combination which is a solution containing either a weak acid or a weak base at a concentration that renders the solution resistant to change in pH. The buffer solution can provide a source of hydrogen cations, which can combine with the nitrite anions to form nitrous acid ($HNO_2$). Nitrous acid can decompose into several products in water. One of these products is nitric oxide. The reactions are summarized below in equations (I), (II) and (III):

$$NaNO_2 \leftrightarrows Na^+ + NO_2^- \quad (I)$$

$$NO_2^- + H^+ \leftrightarrows HNO_2 \quad (II)$$

$$3HNO_2 \leftrightarrows H_2O + H^+ + NO_3^- + 2NO \quad (III)$$

The nitric oxide precursor can include sodium nitrite, which dissociates into sodium cations and nitrite anions, as shown in equation (I). The nitrite anions in the buffer solution can form nitrous acid as shown in equation (II), which can decompose into water, nitrate and hydrogen ions and two molecules of gaseous nitric oxide, as shown in equation (III).

The generated nitric oxide gas formed by the above reactions has a low solubility in the pH buffer combination (e.g., 0.00983 g nitric oxide per liter at 0° C.; 4.6 mL/100 mL at 20° C. in water (Merck Index, 10th Edition, 1983)). The relatively insoluble nitric oxide can be removed from the solution by a transport gas stream to form a therapeutic gas. The transport gas can be 100% oxygen, a mixture of air and oxygen or ambient air. The transport gas stream can be bubbled, otherwise distributed through the solution or swept over the solution. Other byproducts such as, for example, nitrous acid and nitrogen dioxide, can be volatile and can be carried with the transport gas stream along with nitric oxide formed in the reaction.

When delivering nitric oxide for therapeutic use to a mammal, it can be important to avoid delivery of nitrogen dioxide to the mammal. Nitrogen dioxide can be formed by the oxidation of nitric oxide with oxygen. The rate of formation of nitrogen dioxide is proportional to the square power of the nitric oxide concentration and the first power of the oxygen concentration. Reducing the nitric oxide concentration by a factor of ten reduces the nitrogen dioxide concentration by a factor of one hundred. Thus, by limiting the nitric oxide concentration in a therapeutic gas, the therapeutic gas can be substantially devoid of nitrogen dioxide. For example, when nitric oxide concentration in the transport gas is below 100 ppm, the resulting therapeutic gas generated from the nitric oxide precursor in a solution is substantially devoid of nitrogen dioxide.

In certain circumstances, the concentration of nitric oxide generated in the therapeutic gas is controlled, for example, by the concentration of nitric oxide precursor provided to the solution, the concentration of hydrogen cations in the solution, and the characteristics of the pH buffer combination. Other factors that can affect the nitric oxide concentration in the therapeutic gas can include, for example, physical form of the nitric oxide precursor, presence of a reduction-oxidation reaction in an optional gas purifier, and rate of flow of the transport gas through the solution.

The concentrations of hydrogen cations and the nitric oxide precursor can control the rate of generation of nitric oxide. Since the concentration of nitric oxide is low, about 20 to 100 ppm, reaction conditions that increase the concentration of nitric oxide precursor and decrease the concentration of hydrogen ions lead to a stoichiometrically inefficient reaction. Decreasing the concentration of hydrogen ions, for example, by using a weak acid, shifts the equilibrium in equation (II) toward the nitrite anions. A reservoir of nitrite ions can be created such that the nitrous acid concentration is maintained at a relatively constant level.

In certain circumstances, the therapeutic gas can be passed through an optional therapeutic gas purifier. When the therapeutic gas stream contacts the optional therapeutic gas purifier, residual impurities, such as nitrous acid and nitrogen dioxide, are removed from the therapeutic gas stream. The optional gas purifier can include a filter, for example, a semipermeable membrane or barrier, a scrubbing solution, a reduction-oxidation solution, or a pyrolizer. The semi-permeable membrane is a barrier which allows the nitric oxide to pass and retains the impurities. The scrubbing solution is a solution that removes impurities by neutralizing them, for example, a solution of 10% sodium bicarbonate, a 1M ferrous salt solution or an acidified 1M ferrous sulfate solution. A series of aqueous reservoirs can be used to completely decompose the nitrous acid and dissolve any nitric acid or nitrogen dioxide impurities. The reduction-oxidation solution contains a reduction-oxidation agent, which converts impurities completely into nitric oxide. The reduction-oxidation agent can include a ferrous salt. The pyrolizer is a chamber or other component which decomposes the impurities such as nitrous acid and nitrogen dioxide by irradiation or heating. A catalyst, for example, platinum, nickel or silver, can be used to decrease the pyrolysis temperature. For example, the impurities such as nitrous acid and nitrogen dioxide can be passed through a 12 inch long silver tube, ⅛ inch in diameter, heated at 800° C. at a flow rate of 1L/minute. The removal of impurities can be enhanced by using a convoluted or a long path for the bubbling of the therapeutic gas stream through the filter. Additionally, the surface-to-volume ratio of the bubbles can be increased for effective filtration of impurities. For example, a gas sparger can be used to make smaller bubbles. Alternatively, filter media can also be coated onto a filter or walls of a tube, which can produce a dry therapeutic gas stream upon filtration.

A detector can be included in the therapeutic gas delivery system to detect the concentration of nitric oxide in the therapeutic gas stream. The detector can also detect the concentration of nitrogen dioxide in the therapeutic gas, if necessary, and may provide a warning if the nitric oxide concentration is outside a predetermined range or if the concentration of nitrogen dioxide is above a threshold value. Examples of monitoring techniques include chemiluminescence and electrochemical techniques, and are discussed in, for example, in Francoe et al., "Inhaled nitric oxide: Technical Aspects of Administration and Monitoring," *Critical Care Medicine*, 24(4): 782-796 (1998) which is incorporated by reference in its entirety. The presence of nitric oxide can be detected by for example, a modified version of a Thermo-Electron chemiluminescence (CL) detector.

A kit includes the nitric oxide precursor and instructional material describing a method of generating the therapeutic gas and transporting the therapeutic gas in the transport gas. The therapeutic gas including nitric oxide is substantially devoid of impurities such as nitrogen dioxide.

A therapeutic gas can contain at least 1 ppm of nitric oxide. The therapeutic gas can include less than 100 ppm of nitric oxide. For example, the nitric oxide concentration in the therapeutic gas can be from 20 to 100 ppm. The nitric oxide can be released from the precursor over a period of time ranging from 1 minute to 7 days, 2 days to 3 days, or two hours to twenty four hours.

Oxidation-reduction reactions can assist in the production of nitric oxide. For example, a second salt, such as a nitric oxide-releasing reactant, can be added to the solution. A nitric oxide-releasing reactant, for example, an iodide salt or ferrous salt, assists the production of nitric oxide as shown below:

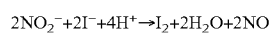

$$2NO_2^- + 2I^- + 4H^+ \rightarrow I_2 + 2H_2O + 2NO$$

or

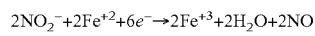

$$2NO_2^- + 2Fe^{+2} + 6e^- \rightarrow 2Fe^{+3} + 2H_2O + 2NO$$

For example, the nitric oxide-releasing reactant can be 1 molar ferrous sulfate solution or 10 wt % aqueous solution of sodium iodide.

Referring to FIG. 1, a nitric oxide delivery system 100 for producing a stream of nitric oxide includes a transport gas pump 105, a restrictor valve 115, a gas inlet tube 135, a gas inlet 130 and nitric oxide precursor receiver 110. The nitric oxide precursor receiver 110 includes nitric oxide precursor contained in a matrix 120 and a reaction solution 190. The reaction solution can include the pH buffer combination which can be used to control the pH of the solution to very close to pH 7 to maintain a concentration of hydrogen ions suitable to control nitric oxide production from the solution. Suitable pH buffers include, for example, combinations of acetic acid and acetate salt (acetic acid/acetate), combinations of hydrochloric acid and chloride salt, combinations of hydrochloric acid and citrate salt (hydrochloric acid/citrate), combinations of citric acid and phosphate salt, combinations of phosphoric acid and phosphate salt (phosphoric acid/phosphate) and combinations of citric acid and citrate salt (citric acid/citrate). A pH within the range of 4.5-7.0, or the range of 6.5-6.9, can be maintained in the solution using the pH buffer combination. The nitric oxide precursor receiver includes a gas outlet 140 connectable to an outlet tube 145, an optional gas purifier 160, a tube 170 and a mask 180. The mask 180 is connectable to a mammal. The flow rate of the transport gas can be controlled by, for example, a restrictor valve 115. For example, the flow rate can be from 1 to 10 liters per minute, 2-8 liters per minute or 2 to 5 liters per minute. The flow rate of the transport gas can be in the range of 1 to 20 liters per minute. The transport gas can be 100% oxygen, a mixture of air and oxygen, or ambient air. The rate of flow of transport gas in the reaction vessel can affect the generation of nitric oxide. Mechanical agitation using, for example, stirring, vibration, sweeping the headspace over the surface of the solution, or bubbling the transport gas through the solution or other methods of agitation can enhance the transfer of nitric oxide to the therapeutic gas.

Referring to FIG. 1, in a general process for delivering nitric oxide, the transport gas pump 105 conveys a stream of transport gas at a specific flow rate into and through the gas inlet tube 135, into inlet 130 and into and through the non-electrolytic nitric oxide precursor receiver 110 which contains the nitric oxide precursor contained in a matrix 120 and reaction solution 190. Nitric oxide is generated in the nitric oxide precursor receiver 110. The stream of transport gas transfers the generated nitric oxide in the therapeutic gas through the gas outlet 140 and through tube 145 into optional gas purifier 160, if necessary. The therapeutic gas including the nitric oxide, is transported in the transport gas into and through tube 170 to mask 180 to the mammal.

The matrix can be a non-reactive support in which the nitric oxide precursor can be contained. The nitric oxide precursor diffuses from the matrix when the matrix, for example, swells, dissolves or erodes in the reaction solution. With changes in these morphological characteristics of the matrix, the mobility of segments in the matrix changes which affects diffusivity of the nitric oxide precursor. Addition of other additives, for example, a polymer, a filler, or a solvent, or modifying reaction factors such as ionic strength, temperature or pH can alter the intermolecular forces, free volume, or glass transition temperature of the matrix, and, consequently, can alter the diffusivity of the nitric oxide precursor. A filler is a substance added to a product to add bulk, weight, viscosity, or strength. The matrix can include nitrite-releasing salt. A nitrite releasing salt assists in the generation of nitric oxide from the nitric oxide precursor. The nitrite releasing salt can include salts of Groups I, II, III, IV, V, VI and VII of the periodic table. For example, the nitrite releasing salt can include a ferrous salt. A nitric oxide precursor can be contained within the matrix, using a number of techniques. Examples of methods for embedding include solvent evaporation, spray drying, solvent extraction and other methods.

The matrix can be, for example, a hydrogel. The hydrogel is a substance which is formed when an organic polymer (natural or synthetic) is cross-linked via covalent, ionic, or hydrogen bonds to create a three-dimensional open-lattice structure, which entraps water molecules to form a gel. The hydrogel can be formed from a polymer, which can include an ionically crosslinkable polysaccharide, synthetic biodegradable, biocompatible polymer, or a protein. Examples of materials which can be used to form the hydrogel can include, for example, a urethane, a polysaccharide such as alginate, a polyphosphazene, a polyacrylate, which are crosslinked ionically, a block copolymer such as PLURONICS™ or TETRONICS™, a polyethylene oxide-polypropylene glycol block copolymer, a polyethylene glycol, or polyethylene glycol which can be crosslinked by temperature or pH. The urethane can be for example, TECOPHILIC, which is a high moisture absorption aliphatic polyether-based polyurethane (commercially available from Thermedics Corporation, Woburn, Mass.). The urethane can include a flexible segment which can be a highly hydrophilic compound, for example, polyethylene glycol or polypropylene glycol. The water soluble flexible segment can be immobilized when bound into the polyurethane molecule to form a polyurethane hydrogel. The polyurethane hydrogel does not fully dissolve, but swells upon hydration to form a gel. The polyurethane hydrogel can absorb two hundred times its weight in water without collapsing. The hydrogel can have a molecular weight of more than 400 g/mol, less than 1 million g/mol or between 400 and 500,000 g/mol, or between 500 g/mol and 3000 g/mol. Other materials can include proteins such as a fibrin, polymers such as a polyvinylpyrrolidone, a urethane, a hyaluronic acid, or a collagen. For example, urethane can be added to provide rigidity to the hydrogel to allow a stronger fabricated shape. For example, a urethane, TECOFLEX 80A solution grade aliphatic urethane (commercially available from Thermedics Inc., Woburn, Mass.) can be added to the hydrogel to retain the post-hydration state of hydrogel and allow longer release times for the nitric oxide. In general, these polymers are at least partially soluble in aqueous solutions, such as water, buffered solutions, or aqueous alcohol solutions. The polymers can have charged side groups. These polymers are either commercially available or can be synthesized using known methods. See, for example, "*Concise Encyclopedia of Polymer Science and Polymeric Amines and Ammonium Salts*," E. Goethals, editor (Pergamen Press, Elmsford, N.Y. 1980).

The matrix can be, for example, a hydrophilic polymer. A hydrophilic polymer can be a polysaccharide containing several sugars with alternating monomer structures and can optionally contain uronic acids. Suitable hydrophilic polymers include guar gum, gum arabic, gum karaya, gum ghatti, locust bean gum, tamarind gum, agar, agarose, carageenan gum, pectin or gluten. The nitric oxide precursor can be contained into the hydrophilic polymer at different loading doses. The loading dose can be more than 0.1%, or less than 25%. For example, the loading dose can be 15% of nitric oxide precursor in the hydrophilic polymer. The matrix and particles of nitric oxide precursor can be directly shaped into, for example, a tablet. The tablet can range in size from 0.01 cm diameter to 5 cm diameter. The tablet can in the range of 0.10 cm to 5 cm in thickness. The tablet can weigh 1 mg to 500 mg. The tablet can range in size from 1 cm diameter×0.5 cm thick and weigh 300 mg. This delivery system can release nitric oxide in a controlled manner over a long time period while also achieving complete dissolution.

Referring to FIG. 1, the matrix 120 can be an agar gel matrix containing 5% (wt/wt) of sodium nitrite which can be placed in the nitric oxide precursor receiver 110. A reaction solution 190 can be placed on the agar gel matrix. The transport gas can flow through and into the nitric oxide precursor receiver and carry the generated nitric oxide gas into gas outlet 140 as the therapeutic gas. The therapeutic gas can pass into and through the optional gas purifier 160 to remove any impurities, if present, through and into tube 170 through mask 180 to the mammal.

Referring to FIG. 2, a matrix can include, for example, shapes that physically immobilize the nitric oxide precursor to control reaction rate of the generation of the nitric oxide. The shape of the matrix can vary depending, for example, on the type of reaction system employed. Examples of the shapes of the matrix include spray dried power, a sphere, a monolith or a three dimensional object. The sphere can include a ball (FIG. 2A), a pebble (FIG. 2B), a microsphere or a pellet. A monolith is a matrix shaped into a column or column containing cells. The monolith can include a single monolith (FIG. 2D), a stacked monolith (FIG. 2H and FIG. 2I) or honeycombed monolith (FIG. 2E). A three dimensional object can include a tube (FIG. 2H), a cylinder (FIG. 2D), a cake (FIG. 2F), a powder, a film (FIG. 2G), an extrudate or a granule. The body geometry and shape of the matrix will be dictated by the circumstances of use. A unitary structure for delivering nitric oxide gas can include a mixture of a matrix and a plurality of nitric oxide precursor particles contained in the matrix. The matrix can include polymers, buffers, salts, fillers or solvent as described above.

Figure 3:
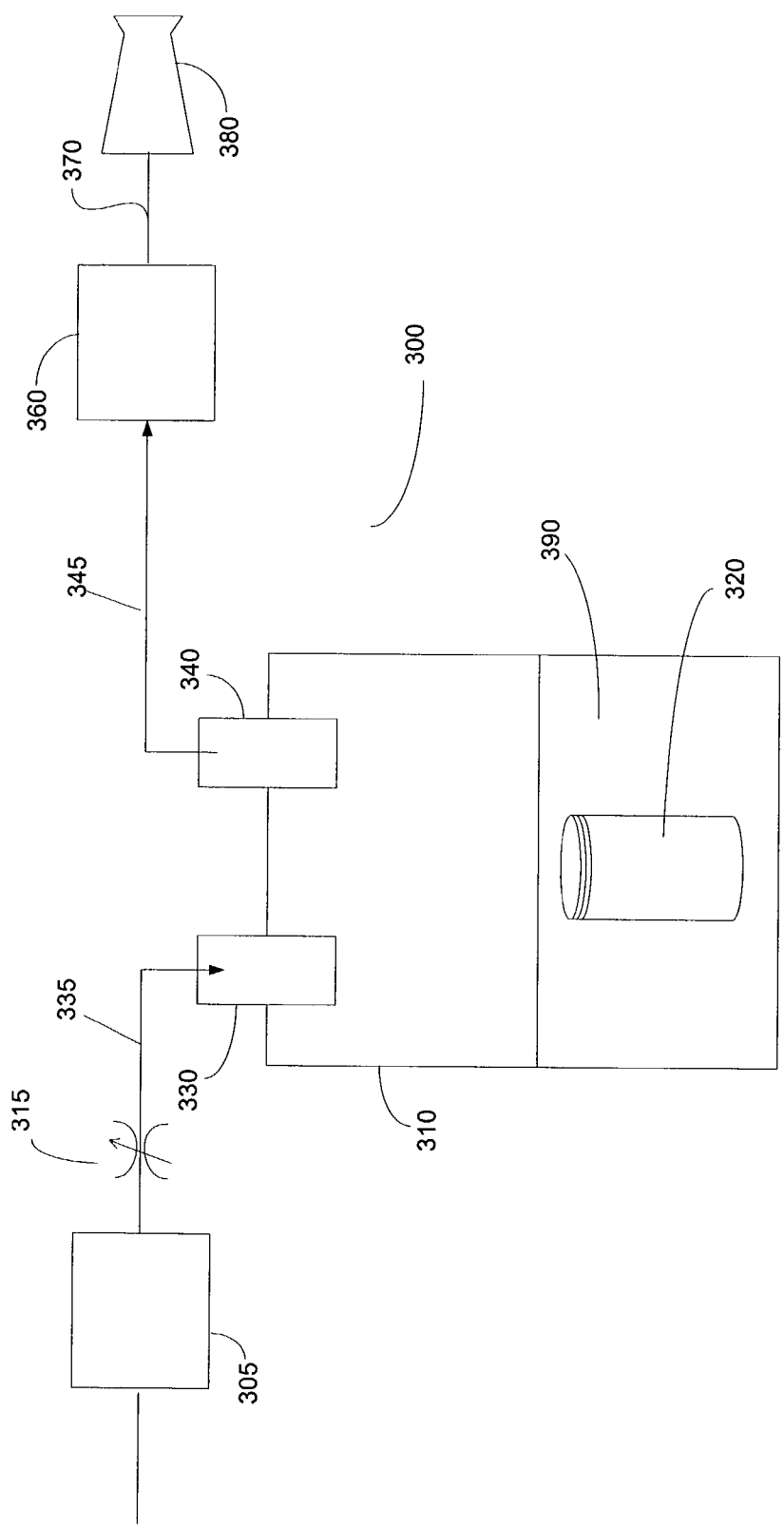
FIG. 3 is a drawing depicting a schematic view of a nitric oxide generation and delivery system.

Referring to FIG. 3, a nitric oxide delivery system 300 for producing a stream of nitric oxide includes a transport gas pump 305, a restrictor valve 315, the nitric oxide precursor receiver 310 with the monolith 320 and a reaction solution 390. The nitric oxide precursor receiver includes a gas inlet tube 335, gas inlet 330, gas outlet 340 connectable to a gas outlet tube 345, an optional gas purifier 360, a tube 370 and a mask 380. The mask 380 is connectable to a mammal. The transport gas pump 305 includes the flow restrictor 315 which controls flow rate of a transport gas.

Referring to FIG. 3, in a general process for delivering nitric oxide, the transport gas pump 305 conveys a stream of transport gas at a specific flow rate, into and through the inlet 330 and into and through the nitric oxide precursor receiver 310, which contains the monolith 320 and reaction solution 390. The monolith 320 can include, for example, the nitric oxide precursor, a nitric oxide releasing agent, or a mixture of the contained nitric oxide precursor and the nitric oxide releasing reagent contained in a matrix. Water, as reaction solution 390, can be introduced into the nitric oxide precursor receiver 310, which initiates the generation of therapeutic gas. The transport gas flows through the nitric oxide precursor receiver and transfers the nitric oxide generated in nitric oxide precursor receiver. A plurality of monoliths can be stacked.

For example, a two-component monolith can be constructed with the nitric oxide precursor (e.g. sodium nitrite) in a first monolith and a second monolith containing the nitric oxide releasing reactant (e.g. ferrous sulfate). The two-component monolith can be placed in the reaction solution to generate low concentrations of nitric oxide. The stream of transport gas transfers the generated nitric oxide as the therapeutic gas into and through outlet 340 into an optional gas purifier 360, if necessary. The therapeutic gas including the nitric oxide is then transported in the transport gas into and through tube 370 to mask 380 to the mammal.

In another approach, controlled-release and delivery of nitric oxide can involve generation of nitric oxide by, for example, electrophoresis. An electrophoresis slab can be filled with an electrophoresis medium, and the fluid medium can be covalently cross-linked or temperature-solidified to form a gel separation medium. A sample can be loaded into a well in the slab gel, and an electric field can be generated to draw the samples through the medium. Electrophoretic migration can depend predominantly on molecular size or on a combination of size and charge and applied voltage.

Figure 4:
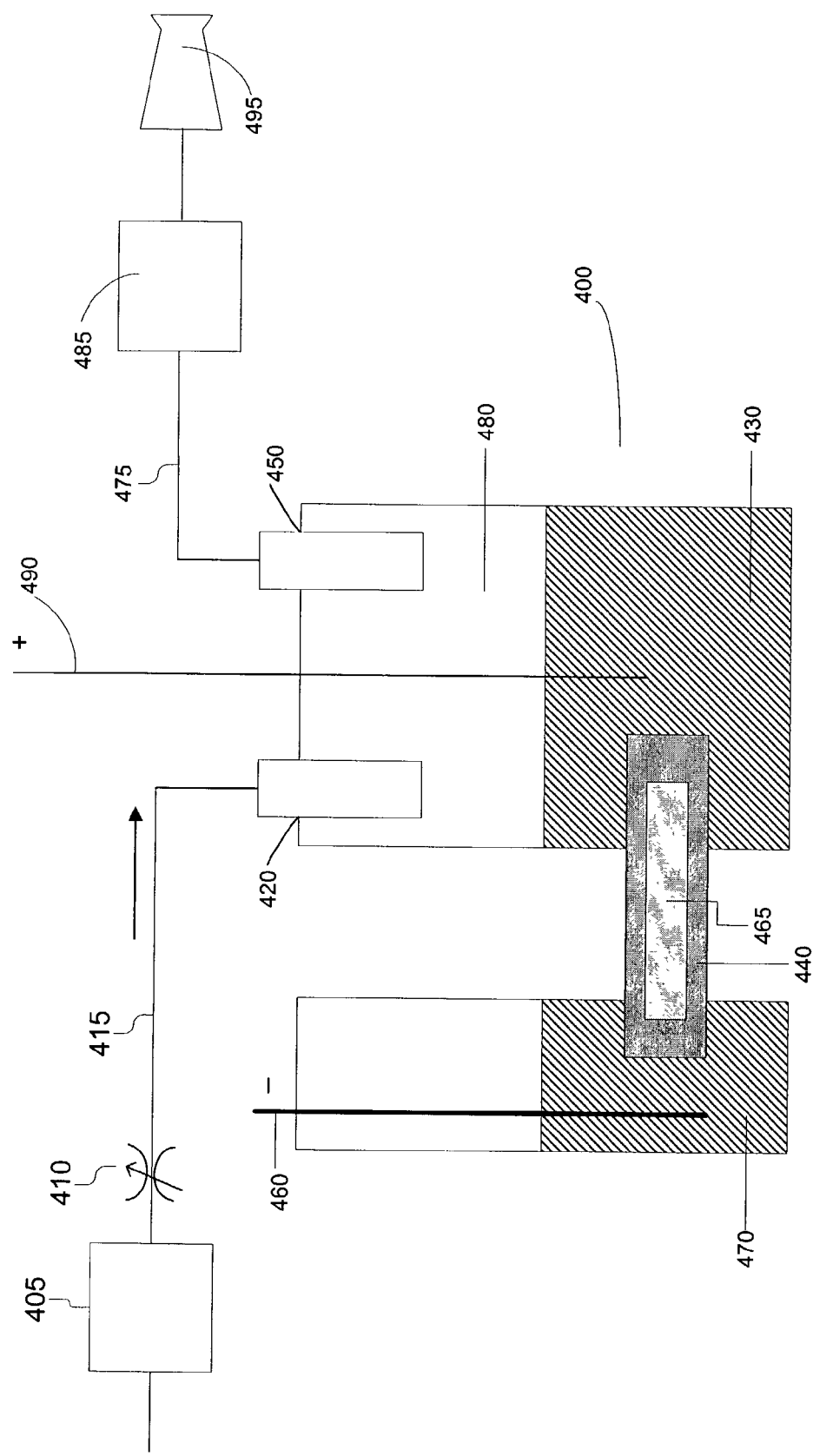
FIG. 4 is a drawing depicting a schematic view of a nitric oxide generation and delivery system.

Controlled-release and delivery of nitric oxide can include, for example, an electrophoresis cell. Referring to FIG. 4, a nitric oxide generation system 400 can include a nitric oxide receiving portion 440, a delivery portion 480, a first electrode 460, and a second electrode 490. The delivery portion 480 can include a reaction chamber 430 including a reaction solution. The nitric oxide receiving portion 440 includes a cavity 465. The generation system 400 can include gas flow controller 405, and an optional gas purifier 485. The gas flow controller 405 includes a flow restrictor 410 which controls flow rate of a transport gas. The generation system 400 includes an inlet gas tube 415, an inlet 420, outlet 450, an outlet tube 475. The outlet tube 475 can be connected to an optional gas purifier 485 which is connectable to a mask 495.

In a general process for generating a stream of nitric oxide, a nitric oxide precursor salt is placed in the nitric oxide receiving portion 440. A reaction solution can be placed in the reaction chamber 430. A voltage can be applied across the first and second electrode, under conditions effective to cause a plurality of nitric oxide precursors to migrate to the reaction chamber 430. The migrated nitric oxide precursors contact the reaction solution in reaction chamber 430 to generate nitric oxide. The transport gas flows from the gas flow controller 405 through the restrictor valve 410, into and through the inlet 420 and transfers the generated nitric oxide in the headspace of 480 as therapeutic gas through and into outlet 450, into outlet tube 475 to an optional gas purifier 485. The optional gas purifier 485 can remove any impurities, if any. The therapeutic gas can be transported from the optional gas purifier 485 through mask 495 to the mammal.

A variety of polymeric materials can be used in the electrophoresis. The polymeric materials can include linear polyacrylamides, polyethylene oxides, dextrans, polyethylene glycols, or polyvinyl alcohols. The appropriate concentration and size of the polymer material included in the medium can depend at least in part on the physical properties and complexity of the sample being analyzed, the properties of the selected polymer or polymers, and the desired delivery rate.

EXAMPLE 1

Using an apparatus depicted in FIG. 1, a nitric oxide precursor, sodium nitrite and nitric oxide releasing salt, ferrous sulfate were dried at 110° C. for 18 hours, combined with 10% fumed silica (Cab-O-Sil M5) and ground to a particle size of 5-10 microns. A hydrogel, urethane resin was dissolved in tetrahydrofuran to produce a lacquer of 30% solids. The finely powdered nitric oxide precursor and nitric oxide releasing salt mixture were suspended in the hydrogel, urethane, of molecular weight 3000 g/mol or 500 g/mol at 20% concentration by weight of the mixture to the urethane to form a solution. The solution was cast in shallow dishes and allowed to dry at 30° C. for several hours. The film was removed from the dish and stored in a dessicator. Sample films were prepared with dried ferrous sulfate, ferrous sulfate as the septahydrate, sodium nitrite and a mixture of sodium nitrite and ferrous sulfate. The reactant concentration was 10 milligrams per square centimeter of film. Varying the length of the hydrogel strips controlled the nitric oxide production. The hydrogel with reactants can be added to a solution containing reactants to release the nitric oxide as shown in Table 1.

TABLE 1

| Hydrogel with reactants | Reaction Solution |
| --- | --- |
| Hydrogel with nitric oxide precursor | Nitric oxide releasing salt in water |
| Hydrogel with nitric oxide releasing salt | Nitrite reactant in water |
| Hydrogel with both nitric oxide precursor and nitric oxide releasing salt | Water |
| Hydrogel I with nitric oxide precursor and Hydrogel II with nitric oxide releasing salt | Water |

EXAMPLE 2

Referring to FIG. 1, an agar gel solution was prepared by dissolving 1 g of Agar powder in 100 mL of boiling water, followed by addition of 5 g of nitric oxide precursor, sodium nitrite. The agar solution (20 mL) was poured into the nitric oxide precursor 110, allowed to cool overnight, and subjected to dissolution study at various reaction conditions as shown in Table 2. Controlled generation of nitric oxide was observed at all reaction conditions. The generation was slower at a pH of 3 as compared to pH of 1. The addition of $FeSO_4$, showed an acceleration in the production of nitric oxide in pH 1 HCl/buffer solution. The nitric oxide rate increased as a function of increasing $FeSO_4$ concentration from 1%, 3% to 5% of $FeSO_4$. Nitric oxide levels were between 10 and 100 ppm in the therapeutic gas.

TABLE 2

| Experiment | Reaction solution |
| --- | --- |
| Experiment 1 | pH 3 phosphate buffer |
| Experiment 2 | pH 1, HCl/KCl buffer |
| Experiment 3 | pH 1 HCl/KCl buffer, 10% $FeSO_4$ |
| Experiment 4 | 1% $FeSO_4$ |
| Experiment 5 | 3% $FeSO_4$ |
| Experiment 6 | 10% $FeSO_4$ |

EXAMPLE 3

Referring to FIG. 4, an agarose gel is doped with a nitric oxide precursor, placed between two buffer solutions and subjected to an applied electrical field as follows. A buffer solution of 50×Tris acetic acid EDTA (TAE) is prepared by adding 242 g Tris base and 57.1 g glacial acetic acid to 100 mL of 0.5 molar EDTA to form a solution. The buffer solution (2 mL) is diluted with 98 mL water to make a solution, 1×TAE. A 1% agarose solution is prepared by adding 5 g sodium nitrite and 0.7 g agarose to 100 mL of 1×TAE at 100° C., while stirring to allow complete dissolution. The solution is allowed to cool to 55° C. and is poured into a suitable mold to form a gel. The gel is then placed in the nitric oxide precusor receiving portion. The reaction solution of buffer 50×TAE is placed at the first and second electrode. An electrical field of 150 VDC is applied to immersed electrodes. The applied electrical field causes the nitric oxide precursor to migrate through the gel and into the reaction chamber to generate nitric oxide. The nitric oxide becomes dispersed in the headspace above the solution and is swept with the transport gas stream to form the therapeutic gas. Their embodiments are within the scope of the following claims.

What is claimed is:

1. A method of manufacturing a unitary structure for delivering nitric oxide comprising: combining a matrix, a nitric oxide releasing agent, and a plurality of nitric oxide precursor particles to form a mixture; shaping the mixture to form a unitary structure, wherein the unitary structure is a stacked monolith that includes at least two columns; and drying the mixture.

2. A process for preparing a formulation for delivering nitric oxide comprising: combining a plurality of the nitric oxide precursor particles and a nitric oxide releasing agent within a hydrophilic matrix to form a mixture; shaping the mixture to form a unitary structure, wherein the unitary structure is a stacked monolith that includes at least two cylinders; and drying the mixture.

3. The process of claim 2 wherein the hydrophilic matrix is a polysaccharide.

4. The process of claim 2 wherein the hydrophilic matrix includes a polymer selected from a group consisting of guar gum, gum arabic, gum karaya, gum ghatti, locust bean gum, tamarind gum, agar, agarose, carageenan gum, pectin and gluten.

5. A method of manufacturing a unitary structure for delivering nitric oxide comprising: combining a nitric oxide releasing agent and a plurality of nitric oxide precursor particles with a polymer solution to form a mixture, cross-linking the polymer, shaping the mixture to form a unitary structure, wherein the unitary structure is a stacked monolith that includes at least two cylinders.

6. A process for preparing a formulation for delivering nitric oxide comprising: combining a plurality of the nitric oxide precursor particles and a nitric oxide releasing agent with a hydrophilic-polymer solution to form a mixture, cross-linking the polymer, shaping the mixture to form a unitary structure, wherein the unitary structure is a stacked monolith that includes at least two cylinders.

\* \* \* \* \*